(12) United States Patent
Valaskovic et al.

(10) Patent No.: US 9,646,815 B2
(45) Date of Patent: May 9, 2017

(54) INTEGRATED NANOSPRAY SYSTEM

(71) Applicant: NEW OBJECTIVE, INC., Woburn, MA (US)

(72) Inventors: Gary Valaskovic, Cambridge, MA (US); Ben Ngo, Malden, MA (US); John P. Devlin, Tewksbury, MA (US); Kurt M. Maw, Salem, MA (US); Ian Schon, Brookline, MA (US)

(73) Assignee: NEW OBJECTIVE, INC., Woburn, CT (US)

( * ) Notice: Subject to any disclaimer, the term of this patent is extended or adjusted under 35 U.S.C. 154(b) by 0 days.

(21) Appl. No.: 14/409,233

(22) PCT Filed: Jun. 5, 2014

(86) PCT No.: PCT/US2014/041033
§ 371 (c)(1),
(2) Date: Dec. 18, 2014

(87) PCT Pub. No.: WO2014/197665
PCT Pub. Date: Dec. 11, 2014

(65) Prior Publication Data
US 2016/0079051 A1    Mar. 17, 2016

Related U.S. Application Data

(60) Provisional application No. 61/832,335, filed on Jun. 7, 2013.

(51) Int. Cl.
*H01J 49/16* (2006.01)
*G01N 30/72* (2006.01)
(Continued)

(52) U.S. Cl.
CPC ........ *H01J 49/165* (2013.01); *G01N 30/7266* (2013.01); *H01J 27/022* (2013.01); *H01J 27/26* (2013.01); *H01J 49/068* (2013.01)

(58) Field of Classification Search
USPC .................................. 250/283, 282, 288, 424
See application file for complete search history.

(56) References Cited

U.S. PATENT DOCUMENTS 6,667,474 B1   12/2003   Abramson et al.
8,753,586 B2 *  6/2014   Prentice .................. B01L 3/563
                                                                137/315.01
(Continued)

FOREIGN PATENT DOCUMENTS

WO    2012148699 A1   11/2012
WO    2013063502 A2    5/2013

OTHER PUBLICATIONS

International Search Report Dated October 29, 2014, Mailed Dec. 5, 2014.

*Primary Examiner* — Phillip A Johnston
(74) *Attorney, Agent, or Firm* — Norris McLaughlin & Marcus P.A.

(57) ABSTRACT

Integrated nanospray ionization package, comprising a nanospray emitter, a push button carriage with button element projecting through a bore in said package, an integral high voltage contact pin, a bore in said package for reversible protrusion of the nanospray emitter, a push-and-retract spring mechanism in which the range of forward motion of the emitter is not dependent on range of travel of the said button, and then upon actuation of said button element and spring element for retraction of said nanospray emitter, said nanospray emitter is pushed forward to establish electrical contact, and upon release of said button retracts and breaks the electrical contact.

11 Claims, 16 Drawing Sheets

Exploded schematic view

(51) Int. Cl.
*H01J 27/02* (2006.01)
*H01J 27/26* (2006.01)
*H01J 49/06* (2006.01)

(56) References Cited

U.S. PATENT DOCUMENTS

2011/0085852 A1 4/2011 Ferrara
2012/0115213 A1 5/2012 Hofstadler et al.

\* cited by examiner

Fig. 1 Exploded schematic view

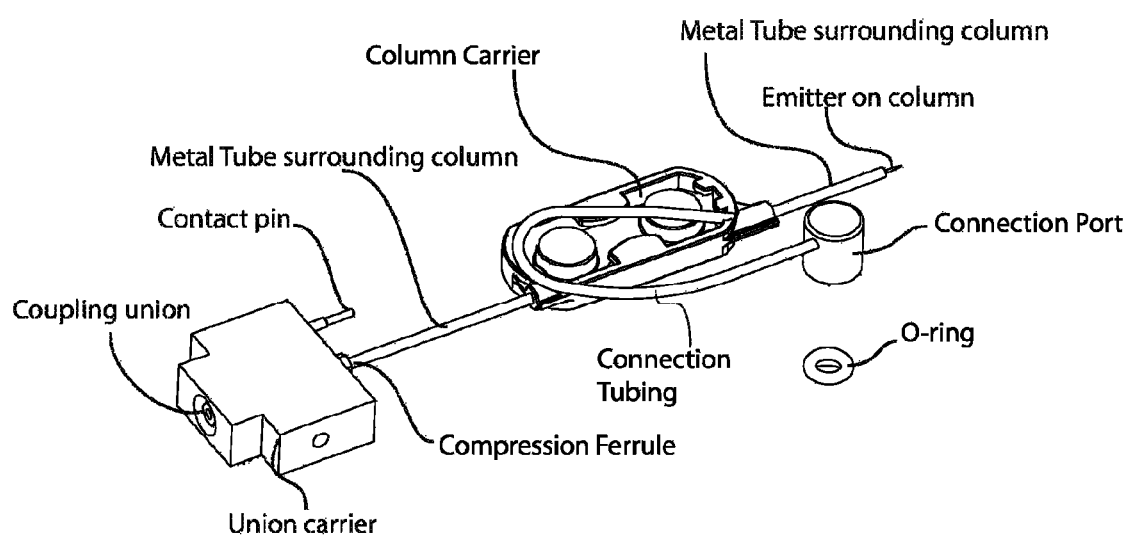
Figure 14 - The Column Mangement System

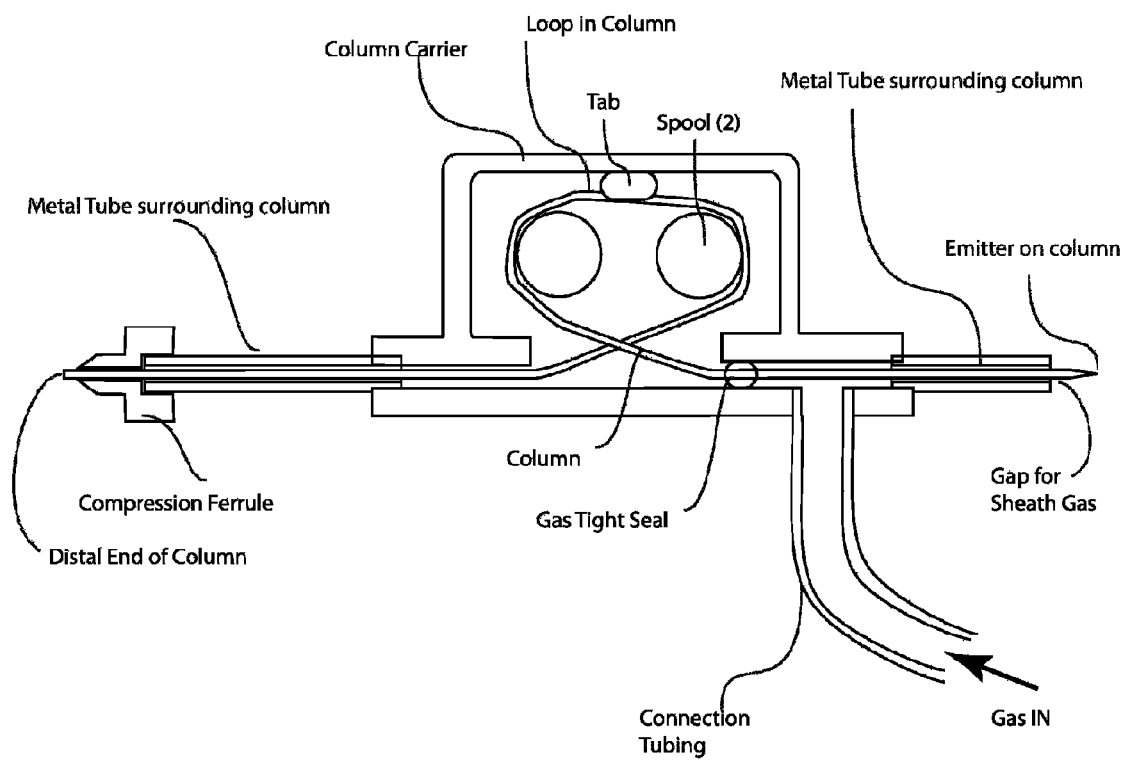
Fig 15 - Cross section, schematic view of column management system

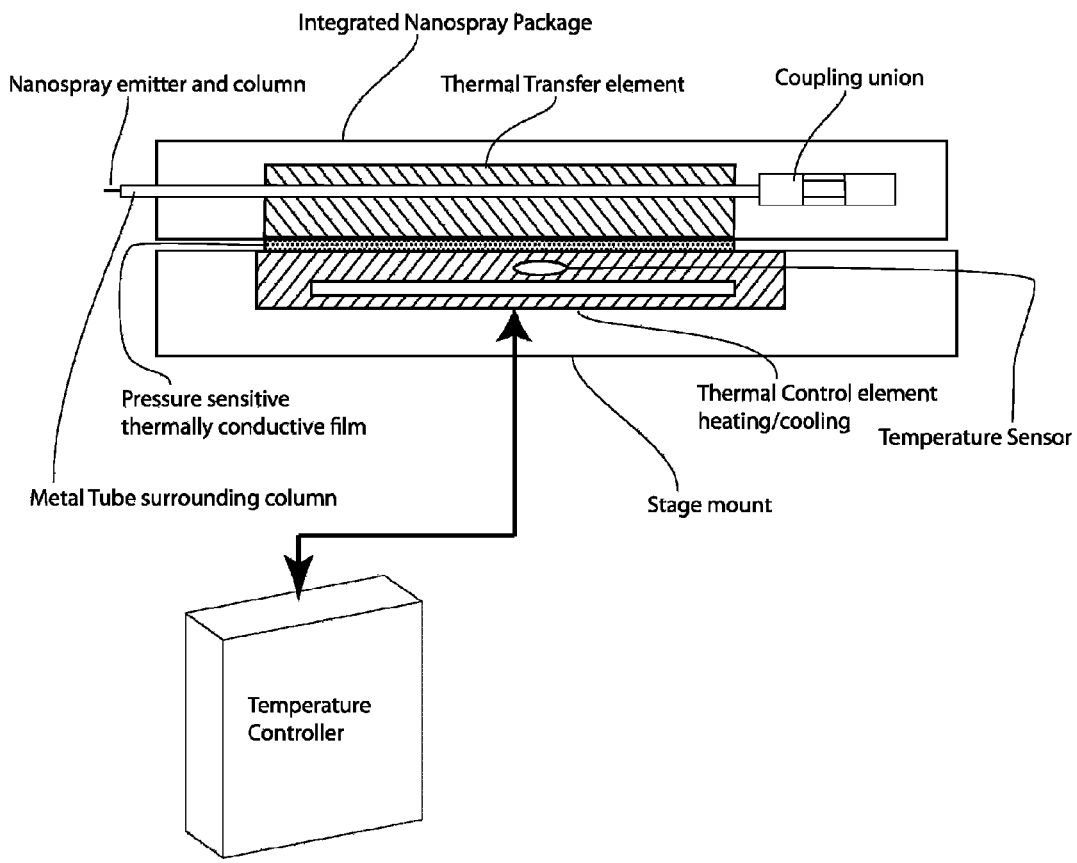
Figure 16. Simplified sectional schematic view of the elements involved in temperature control.

INTEGRATED NANOSPRAY SYSTEM

This is a 371 of PCT/US2014/041033 filed 5 Jun. 2014, which claims priority benefit U.S. Provisional Application 61/832,325 filed 7 Jun. 2013.

This application pertains to an apparatus comprising a novel system for enabling the coupling of liquid chromatography to mass spectrometry and related techniques for the chemical analysis of complex mixtures. The principle utility of the invention is in the area of chemical analysis by electrospray ionization mass spectrometry (ESI-MS). It is particularly well suited, but not limited to, the biochemical analysis of samples of biological origin. It is particularly well suited, but not limited to, the identification and quantification of biomolecules such as proteins and peptides, xenobiotic compounds (drug like molecules), or metabolites present in biological tissues and/or fluids by ESI-MS.

BACKGROUND OF THE INVENTION

Miniaturization of chemical analysis is a highly active area of intense scientific research. Much of the research is driven by the health and life sciences, where miniaturization has the capacity to revolutionize the diagnosis and treatment of disease [Yager et. Al Nature 2006, 442, 412-418; Chin, Linder, Sia Lab Chip, 2007, 7, 41-57]. Central to this theme is the miniaturization of processes and procedures that occur in conventional chemical and biological laboratories. These activities include sampling, storage, sample treatment, separation, detection, and analysis. Miniaturization uses less sample, offers superior detection sensitivity, and has the potential to greatly reduce the costs of laboratory environment, labor, and materials. Efforts at miniaturization have focused primarily on the implementation of so-called microfluidic "lab-on-chip" devices [Chin, Linder, Sia, Lab Chip, 2007, 7, 41-57], although more conventional methods, such as lateral flow chromatography, have also been reduced in scale [Yager et. Al Nature 2006, 442, 412-418].

A particularly promising analytical technology for medical diagnostics from biological tissues and fluids is liquid chromatography coupled to mass spectrometry (LC-MS) [Hoofnagle, Clin. Chem. 2010, 56, 161-164; Anderson Clin. Chem. 2010, 56, 177-185]. LC-MS is a powerful method, but requires a highly complex analytical system. Current state-of-the-art practice requires expert level training of staff, together with a significant investment in laboratory infrastructure. Centralized laboratory resources coupled together with remote sampling of patient populations is a common solution to meet these multiple requirements.

Electrospray ionization is a well-established method to ionize liquid samples for chemical analysis by mass spectrometry. Nanoelectrospray ionization, also referred to as nanospray, is a miniaturized low-flow and low-volume variant of electrospray ionization. Nanospray has been shown to offer superior sensitivity and selectivity compared to conventional electrospray ionization. Various methods exist in the prior art for using nanospray for the on-line analysis of flowing liquid streams, e.g. the effluent from liquid chromatography.

A commonly employed apparatus for on-line nanospray utilizes a nanospray emitter fabricated from a tube, typically 50 to 300 µm inside diameter (ID), having a finely tapered end in which the ID tapers to a 1-20 µm ID orifice. The tapered end is referred to as the proximal end. A high voltage (1-4 kV) is applied to the liquid mobile phase resulting in an electrically charged aerosol emitting from the proximal end during the electrospray process. Some portion of the generated charged aerosol is collected by the inlet orifice of the mass spectrometer for chemical analysis.

Emitters are generally fabricated from tubing made from borosilicate glass, fused-silica, or fused quartz, although other materials including polymers and metals have been employed. The non-tapered end is referred to as the distal end, and is the end of the emitter through with sample and mobile phase enter the emitter. Suitable emitters may contain a sorbent material within the inner bore of the tube for use as a chromatography column for separations or analyte capture and purification, such as that described by U.S. Pat. No. 5,572,023 to Caprioli.

A significant challenge for successful on-line nanospray is multi-fold. These methods are typically time consuming, expensive, and/or require a great deal of hand manipulation and fine motor skills. The nanospray emitters are fairly delicate and fragile. The small ID's for the emitters (<20 µm) require the use of specialized tools. Expert level training is usually required for successful application of the technique. Making fluidic connections that are both leak-free and capable of withstanding high internal operating pressure with tubing that is on the order of 100 µm (0.004")ID and smaller requires a significant investment in operator training. Improper assembly often results in either clogging of tubing or leaks that often go undetected.

Thus there is a significant need for a miniaturized system providing high chromatographic performance and high analytical sensitivity combined with robustness and ease of use for and analysis of samples by liquid chromatography and nanospray ionization mass spectrometry. It is particularly desirable that the system be easy-to-use, be low cost, and offer high throughput. It should be usable with a minimum of specialized laboratory equipment, preferably require only those tools commonly found in a clinical laboratory or hospital environment.

SUMMARY OF THE INVENTION

The present invention addresses these issues by combining desirable aspects of conventional nanobore LC with a novel approach for combining the required elements for conducting the analysis into an integrated package for implementation on the ionization source of the mass spectrometer. There are two main physical assemblies to the invention: (1) the integrated nanospray package and (2) the ionization source mount.

The integrated nanospray package contains and houses the essential elements comprising: a fluidic connection (preferably a fluidic coupling union), a high-voltage electrically conductive element in direct contact with the mobile phase as it flows into through the system, a packed bed chromatography column for liquid phase chemical separation, and the electrospray ionization emitter to enable chemical analysis by atmospheric pressure ionization mass spectrometry. The novel aspect of the invention relates to how these elements are combined together and put into practice.

The integrated nanospray package and ionization source mount together have the following principle novel and inventive features:

(A) The integrated package and the ionization source mount share complementary design features that ensure (1) a stepwise engagement process that locates both integrated package position and electrical contact with the high-voltage provided by the source mount ensuring proper operation and (2) reliable and repeatable positioning of the nanospray emitter with respect to the mass spectrometer inlet to which the source mount is attached.

(B) The integrated package and the source mount share complementary design features that ensure the emitter is engaged and locked into a protruding and exposed operating position only when the integrated package is mounted on the source of the mass spectrometer. When the integrated package is removed from the source, the emitter automatically retracts into the body of the package, protecting the emitter from damage or inadvertent alteration. When the emitter is in the forward spray position, the high voltage contact is established.

(C) The integrated package contains features and elements that enable the application of a co-axial sheath gas to support the pneumatic nebulization of fluid exiting the nanospray emitter. Such features may be enabled by the (reversible) addition of a modular assembly that modifies the operation of the nanospray emitter, or through the integration of these features into the integrated package itself. The modular assembly attaches to the proximal end of the integrated package yielding two primary functions: (1) allow for the addition of a co-axial pressurized nebulization gas around the outer surface of the nanospray emitter that exits the front of integrated package in the direction of the emitter and (2) provide a means for thermal and/or electrical contact with the body of the emitter and/or any material surrounding the emitter or in immediate contact with the proximal end of the emitter. The modular assembly may be readily and reversibly added or removed from the integrated package either during the manufacturing stage or by the end-user at time of use. As noted such features of the modular assembly may be preferably integrated into the source mount, so that these may be enabled when the integrated package is in use on the source mount. These added features, such as the addition of co-axial sheath gas to aid in nebulization are typically under user selection and control. The use of co-axial sheath gas to support nebulization and ionization is well known in the prior art (see Caprioli U.S. Pat. No. 5,572,023).

(D) The integrated package contains a multi-layer, composite, thermally conductive element housed within a thermally insulating body. The conductive element is in contact with the chromatography column and nanospray emitter body, and provides for thermal communication between the interior components (the column, emitter etc.) and the environment immediately exterior to the integrated package. This enables a low-cost method to control the temperature of the chromatography column and nanospray emitter inside the integrated package. This eliminates the costly need to integrate a temperature control element, such as a heating or cooling element, directly within the body of the integrated package. The temperature control element, which for example would be comprised of an electrical heating element and a temperature sensor, and temperature controller, are best placed within the body of the source mount and the heating element is in contact with the thermal conductive element of the integrated package. Thus the economically costly elements of the heater, sensor, and controller are restricted to the ionization source, which is a non-consumable and durable good. Thus the cost of the integrated package is reduced and minimized. The invention makes it possible to pre-heat the column prior to use since the thermally conductive components are in sliding contact with the heating/cooling device rather than direct integration.

Detailed Description

BRIEF DESCRIPTION OF THE DRAWINGS

FIG. 14. is an isometric view of the sub-assembly comprised of the column management system.

FIG. 15. is a simplified cross-section schematic of the column management system showing the routing of the column and sheath gas tubing.

FIG. 16. is a simplified cross-section schematic of the integrated nanospray package and the stage on the source mount showing thermal transfer elements involved in temperature control of the package interior.

FIG. 1 shows an exploded view of the components comprising the integrated nanospray package. The interior components of the integrated package of FIG. 1 include: a push-button carriage with a protruding cylindrical button element, a push spring, an electrically conductive coupling union with compression ferrules, a chromatography column with a tapered electrospray emitter on it's proximal end, a union carrier that is electrically conductive and having a bore to accept the coupling union and column, a retraction spring, a magnet, an electrical contact pin in electrical contact with the union carrier, a set screw to hold the coupling union inside the bore of the union carrier, a bottom assembly cover and a top assembly cover. Particularly suitable forms for the chromatography column and nanospray emitter have been described in the prior art (Caprioli U.S. Pat. No. 5,572,023) and fabricated as described by Valaskovic in U.S. Pat. Nos. 5,997,746 and 6,190,559.

Both the top and bottom assembly covers contain elements to accept the button carriage, union carrier with union and column, the push and retraction springs, a notch or semi-circular hole in the front face to allow the column and emitter to protrude from the body of the integrated assembly. The coupling union and union carrier are preferably made of an electrically conductive metal such as aluminum, stainless steel, or most preferably gold coated stainless steel. The ferrules used in the coupling union may be made of metal or polymer, but are preferably made from an electrically insulating polymer such as polyether-ether ketone (PEEK). This serves to isolate the metal tube surrounding the column and nanospray emitter from being exposed to the high voltage present on the coupling union when the integrated package is in use.

Figure 1:
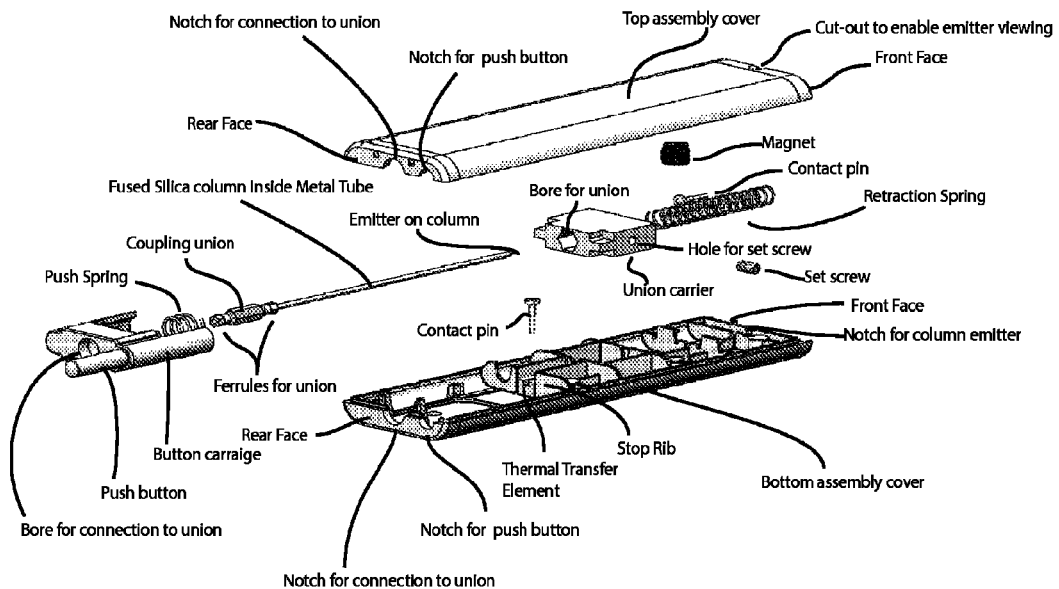
FIG. 1. is an isometric, exploded, view of the integrated nanospray package.
Figure 2:
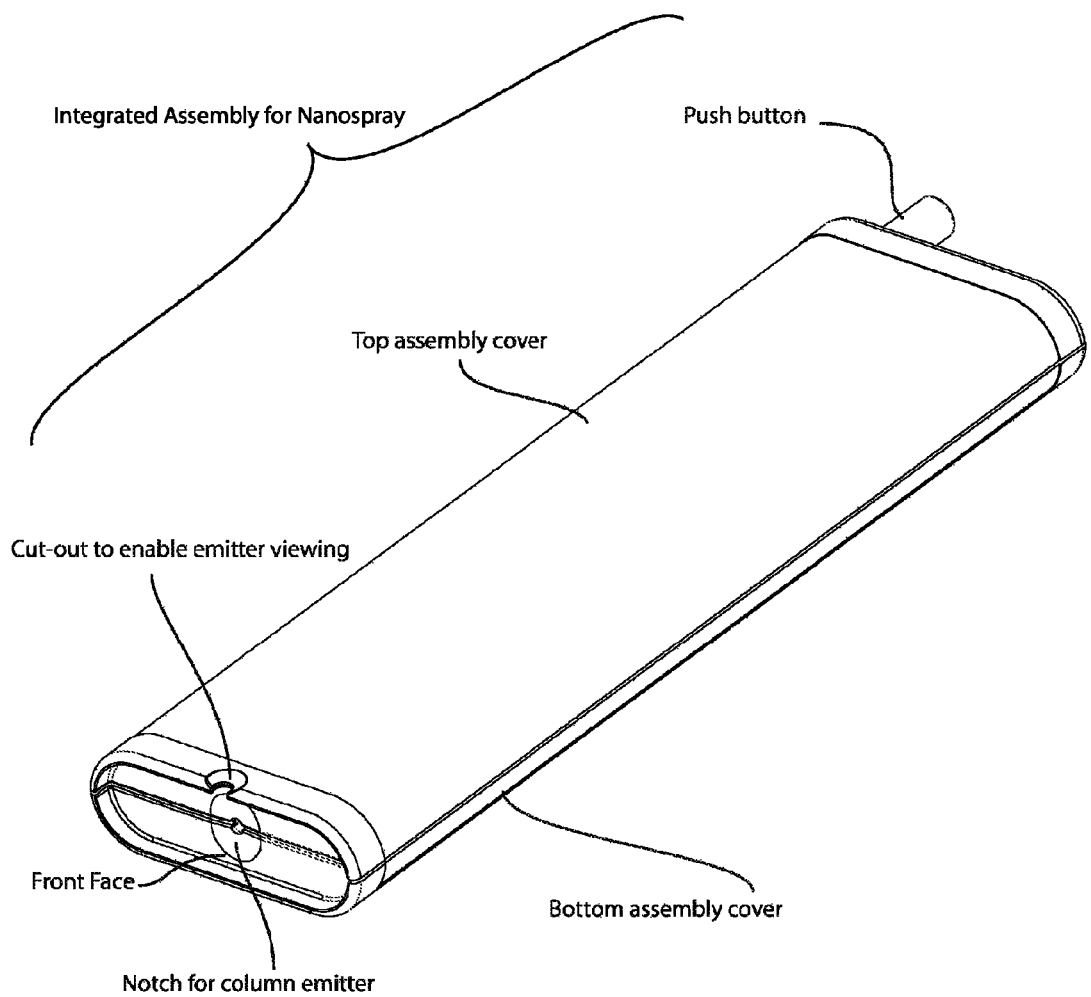
FIG. 2. is an isometric top view of the assembled integrated nanospray package.
Figure 3:
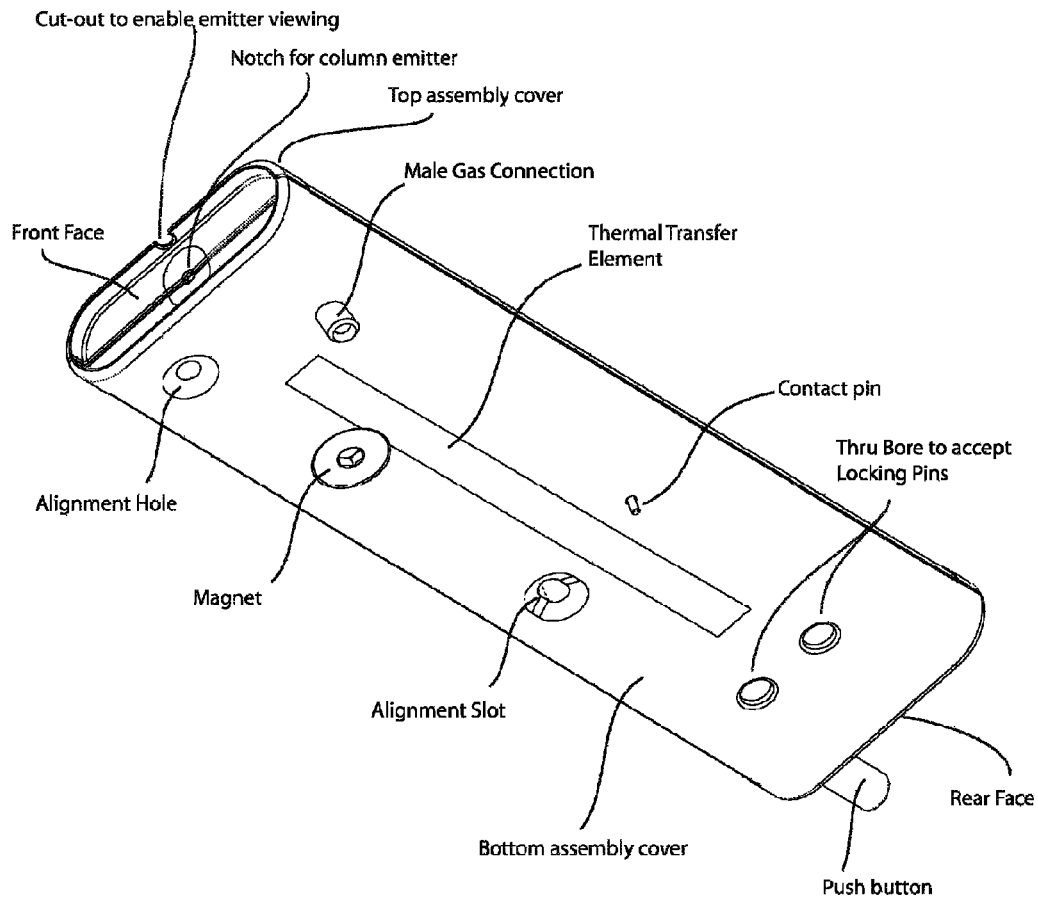
FIG. 3. is an isometric bottom view of the assembled integrated nanospray package.

FIG. 2 shows representative isometric views of the assembled integrated package from the top-side and FIG. 3 from the bottom side. On FIG. 3 the bottom surface of the thermal transfer element is visible. The upper and lower bodies of the integrated package are preferably made from electrically and thermally insulating materials such as polymers or polymer composites. Preferable materials for construction include: nylon, polyethylene, polystyrene, acrylonitrile butadiene styrene (ABS), polyether-ether ketone (PEEK), and polyetherimide. The thermal transfer element shown in FIG. 1 and FIG. 3 is preferably made from a thermally conductive material. Suitable materials include metals such as aluminum and copper, and thermally conductive polymers. The thermal transfer element has a cross sectional profile that enables close physical contact with the chromatography column housed within the package. Suitable profiles include a cylindrical hollow tube or a square-cut trough. The column rests in the hollow of the tube or trough.

Figure 4:
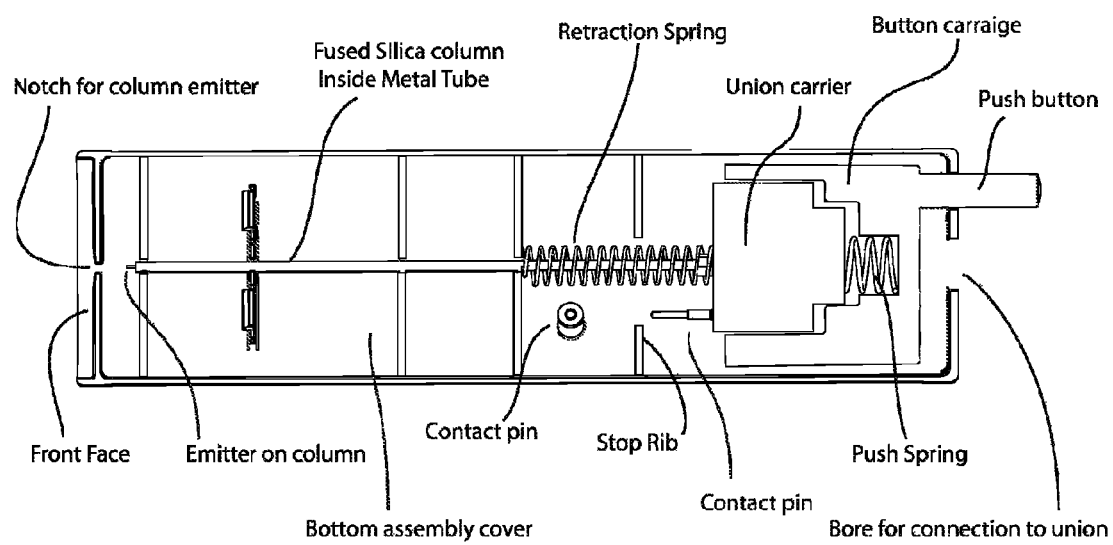
FIG. 4. is a simplified schematic sectional view of the integrated nanospray package with internal components in the non-operating, retracted, position.
Figure 5:
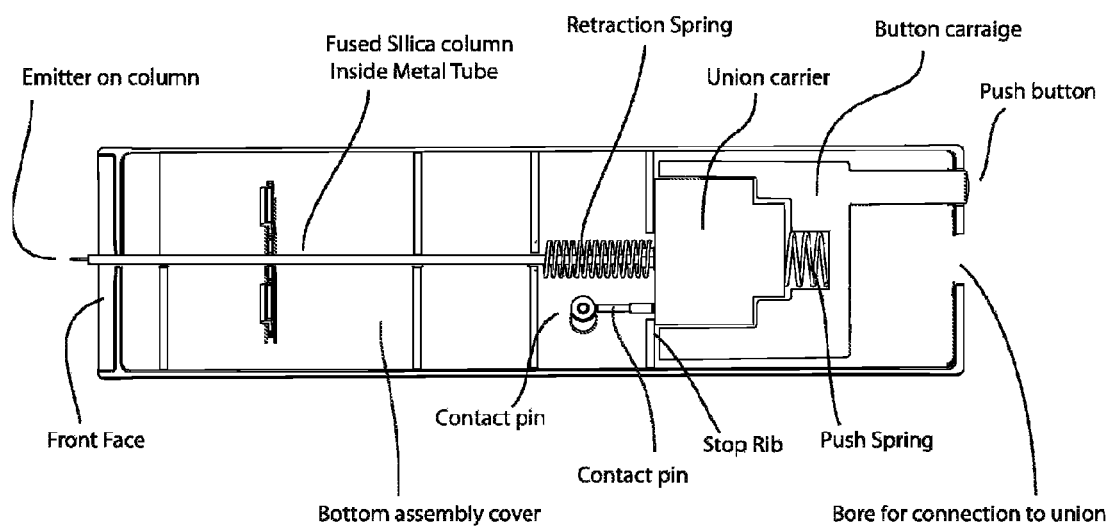
FIG. 5. is a simplified schematic sectional view of the integrated nanospray package with internal components in the operating, forward, position.

FIG. 4 shows the position of the internal components when the button carriage is not pressed. In this position the nanospray emitter is positioned within the recess of the integrated package, and is safe from physical harm or alteration. The relatively greater compressive force of the retraction spring, relative to the push spring, inside the package maintains this condition. FIG. 5 shows the position of the internal components when the button is pressed. Pressing the protruding button towards the body of the assembly on the rear side of the integrated package causes the push spring to compress. The compressive force is transmitted through the push spring to the union carrier so that the elements held by the carrier, namely the union, column, and set-screw move forward. The retraction spring is compressed during this operation. As the button is pushed the union carrier moves forward until its forward face makes contact with a stop rib contained on the body of the lower assembly cover. At this point, the emitter end of the chromatography column is in the desired operating position and is protruding from the forward front face of the assembled top and bottom covers. Because the button carriage does not contact the union carrier directly, further forward motion of the button carriage will create no additional movement of the union carrier and attached elements. When the pressure on the button is removed, the greater force of the retraction spring overcomes the smaller compressive force of the push spring. The action of the retraction spring forces the union carrier, and its attached elements, back into the rearward position with the proximal emitter end of the column retracted into the body of the assembly. This action also (slightly) compresses the push spring. This force of the push spring is transmitted through to the button carriage, pushing the button into a fully extended position from the rear face of the integrated package. In this mode of action, the column and emitter are in the forward operating position only when the force is applied to the button. Releasing the force on the button enables automatic retraction of the column and emitter. This enables a convenient way for visual inspection of the emitter, yet preserves the protection when not in use. In this preferred embodiment, the emitter can only be locked into the forward spray position when the integrated assembly is positioned and engaged on the stage of the source mount as described below.

Figure 6:
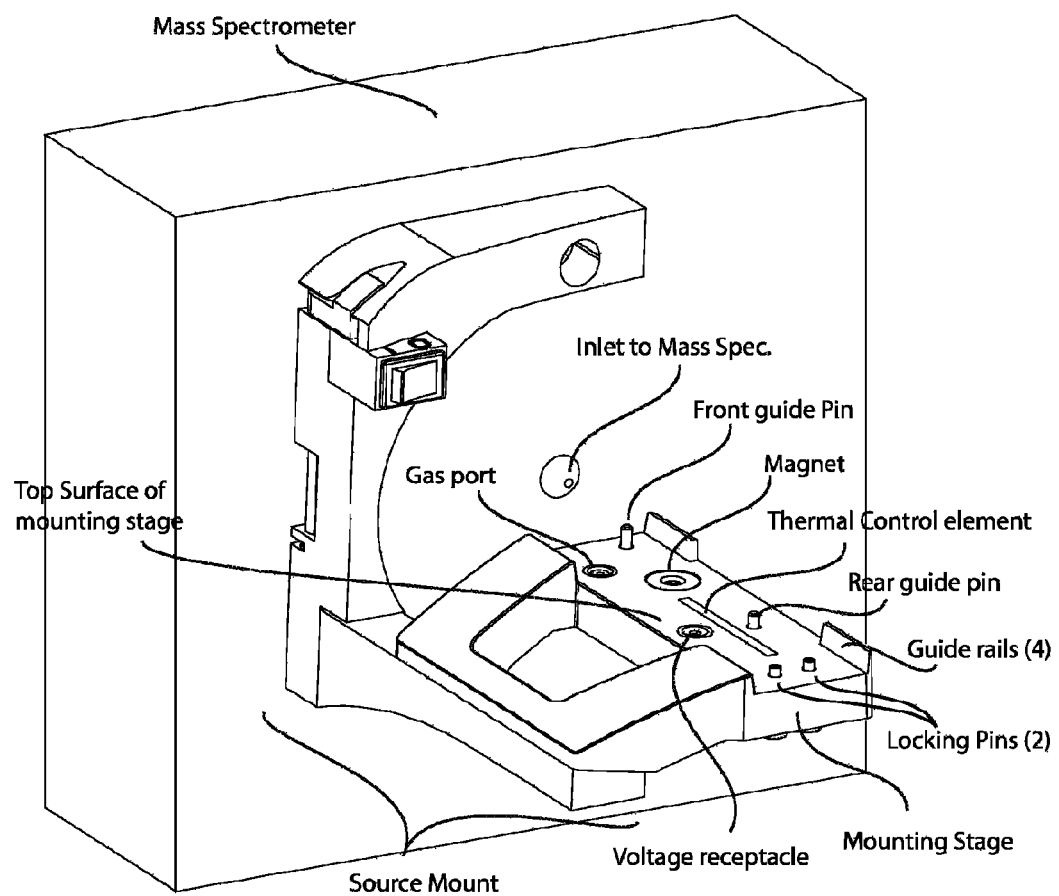
FIG. 6. is a schematic isometric view of the source mount on the body of a mass spectrometer.

FIG. 6 shows receiving stage of the source mount designed to accept the assembled package. While there are many suitable configurations for such a mechanical engagement, the most preferred embodiment of receiving stage described herein is designed to force a particular order of engagement between the stage and the integrated package that reduces the variability of placement between individual practitioners of the method and apparatus. The additional functions of the receiving stage are multi-fold: The stage acts as a physical interface between the integrated package and the atmospheric pressure inlet of the mass spectrometer or other chemical analytical detector, that is capable of analyzing electrospray generated ions. The receiving stage properly positions the assembled package, so that when engaged, the electrospray emitter is in an appropriate position to generate an electrospray suitable for capture by the vacuum system inlet of the mass spectrometer. The receiving stage provides the necessary electrical connection for the delivery of high voltage (typically and preferably in the range of 1 to 5 kV, of either positive or negative polarity relative to ground) to the contact pin on the underside of the integrated package.

The receiving stage also contains design elements to provide for gas flow in support of the application of co-axial sheath gas. This is preferably in the form of a quick connect gas-tight tube, that mates between the gas receiving elements of the integrated package or modular assembly. The quick-connect format means that no nuts or ferrules need to be screw tightened in the connection and mating process. In a preferred embodiment, this takes the form of a recessed, female tapered receiving port on the top face of the stage that contains an elastomer o-ring seal. This recessed female port, mates with a male tube that protrudes from the base of the modular assembly, or in the case where the elements of the modular assembly are contained within the integrated package, from the base of the integral package itself.

The o-ring provides for a gas-tight connection as the outer surface of the male tube contacts and fits tightly within the inner surface of the o-ring. The magnet elements contained in the source mount and integrated package create sufficient force so that the o-ring seals between the male and female tubes. The female tube makes connection to a source of gas, such as oxygen, argon, helium, sulfur hexaflouride, nitrogen, or compressed air of sufficient pressure (typically 10-80 psi) for the support of co-axial nebulization, which is well known in the art of electrospray ionization (see Caprioli U.S. Pat. No. 5,572,023). It is also noted that the design of the male port on the integrated package, and a female port on the mounting stage, may be inverted so that the stage mount has a male connection, and the integrated package a complementary female port. This embodiment is equally preferred.

Figure 8:
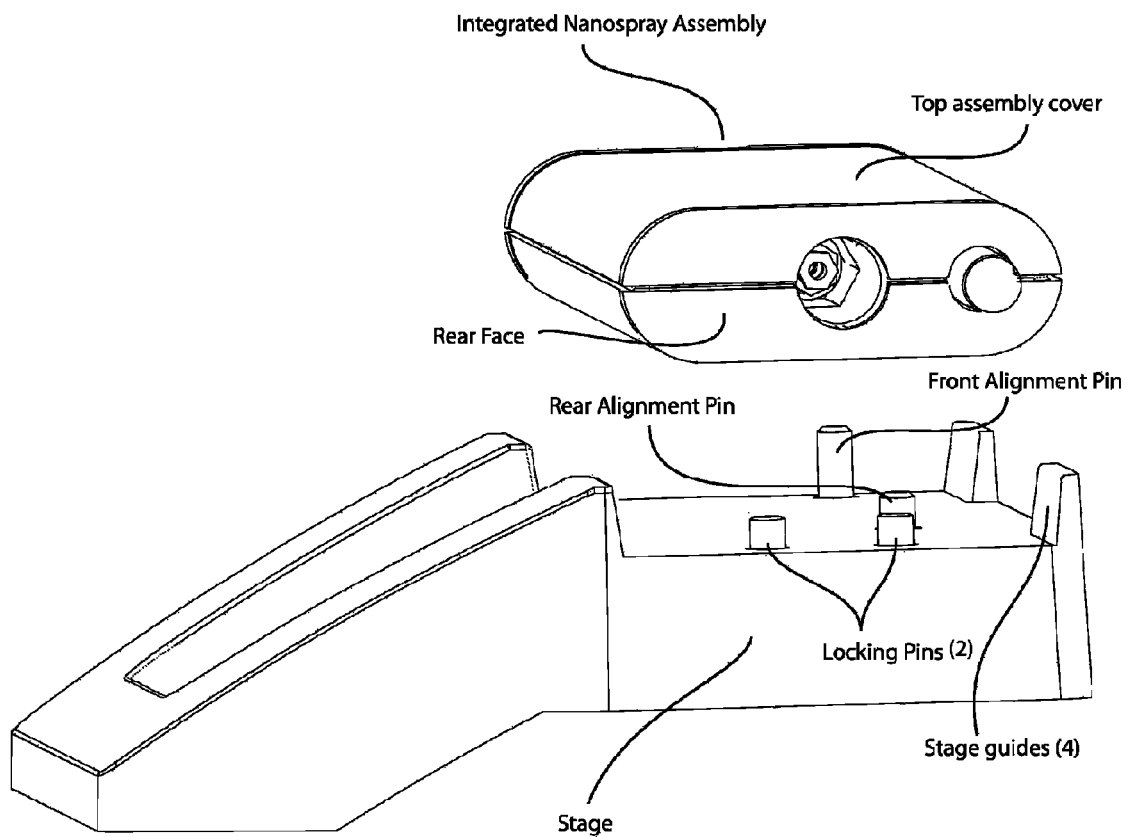
FIG. 8. is a simplified isometric view of the integrated package above the stage of the source mount, before the two sub-assemblies are engaged.

FIG. 8 Shows the main elements that enable and control the docking of the integrated assembly on the stage of the source mount. The stage contains four stage guides, a front alignment pin, and rear alignment pin and two locking pins. The purpose of the stage guides is to offer visual clues, and physical guidance as the operator places an integrated package into position. The front alignment pin is the tallest feature on the stage and is roughly the height of the stage guides above the surface of the stage. The rear pin, is relatively lower, and protrudes approx. ⅔ the distance above the stage surface of that represented by the front pin. The locking pins protrude less than the rear pin, and approx. the height of the front pin. The front pin mates with the alignment hole visible in FIG. 3. on the underside of the package. The rear pin mates with the alignment slot, also visible on FIG. 3. The locking pins mate with the thru bores in the body of the package, also seen on FIG. 3.

Figure 7:
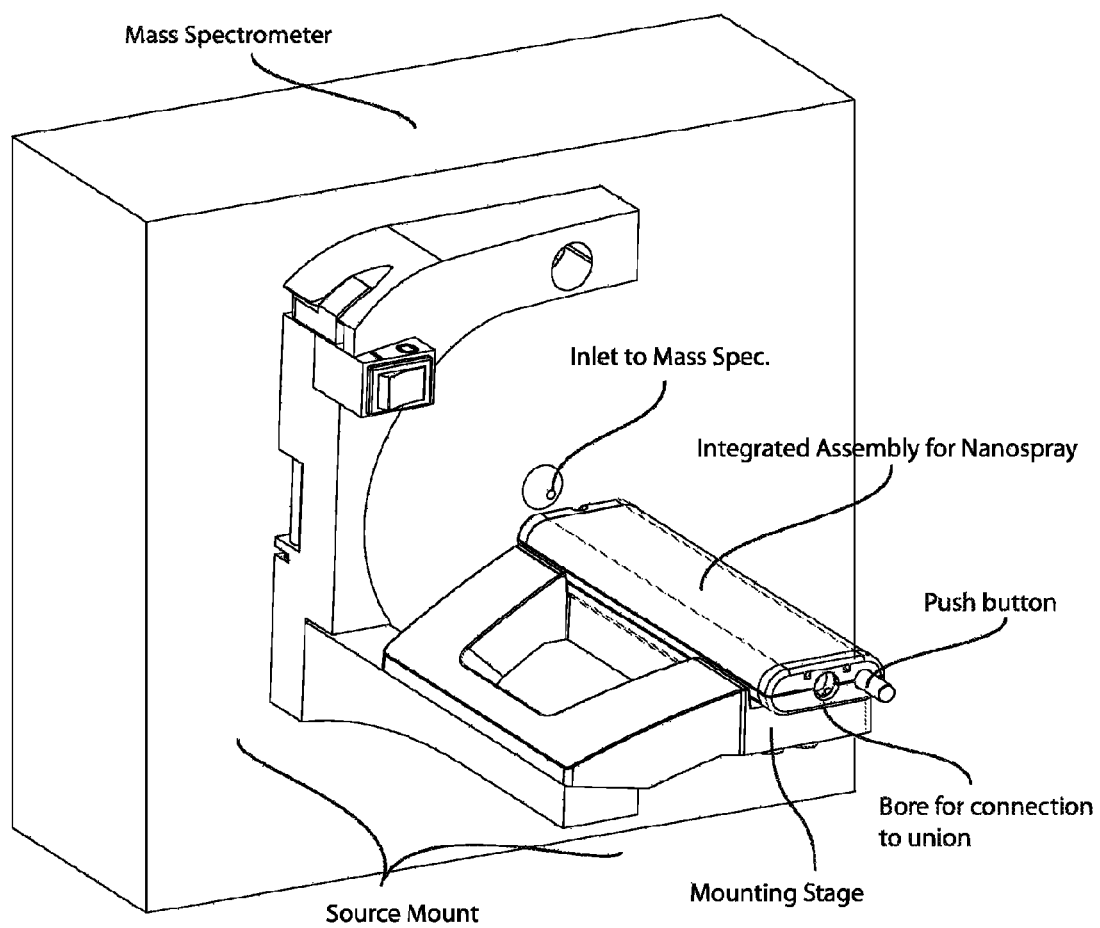
FIG. 7. illustrates the integrated nanospray package ready for use on the source mount.
Figure 9:
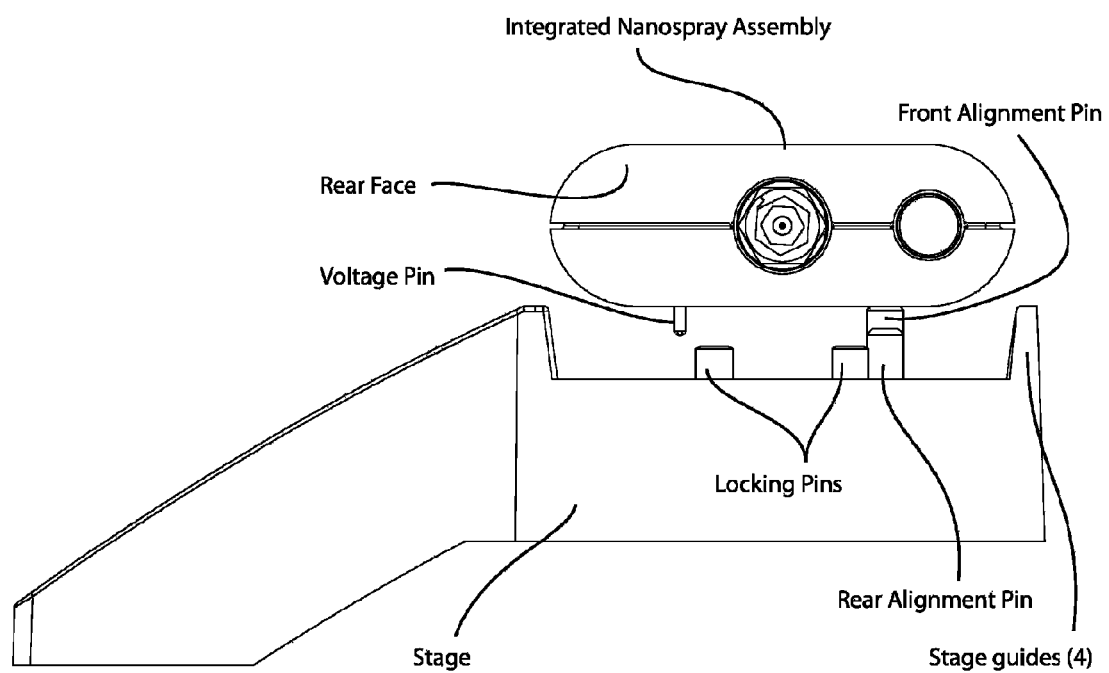
FIG. 9. is a simplified view, from the rear face, of the first step of engagement with the front alignment pin of the stage.
Figure 10:
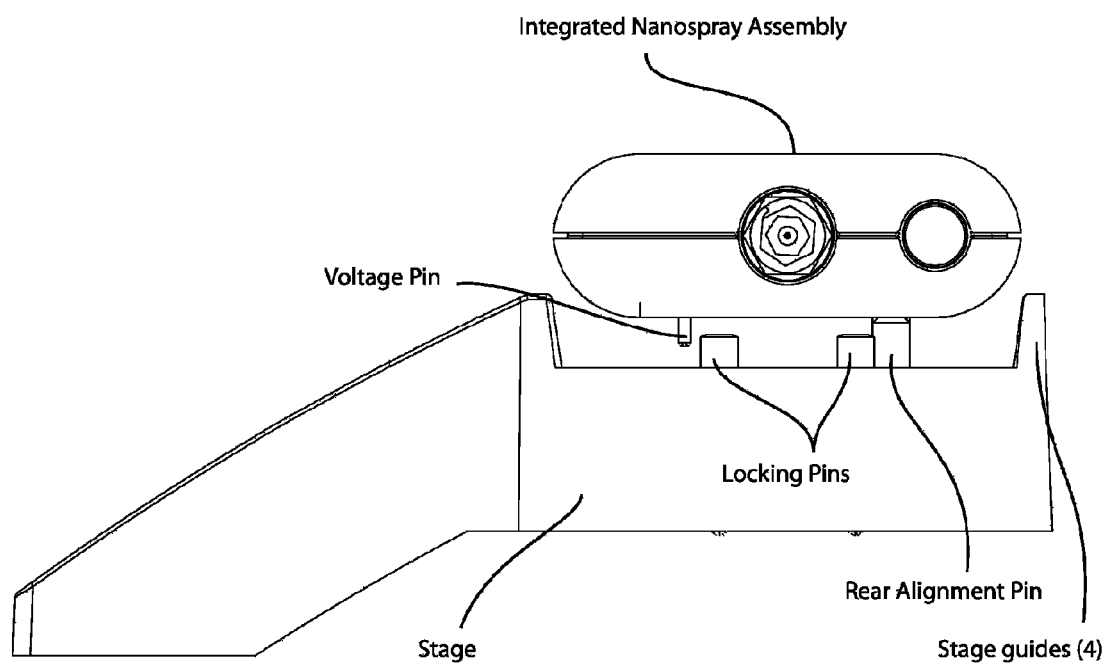
FIG. 10. is a simplified view, from the rear face, of the second step of engagement with the rear alignment pin of the stage.
Figure 11:
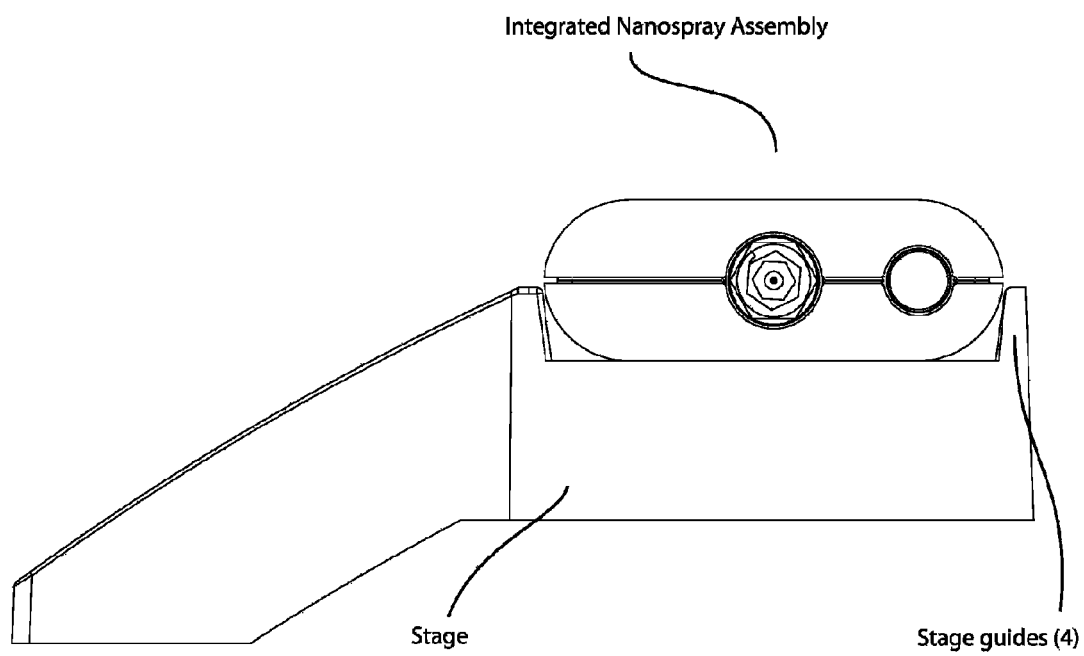
FIG. 11. is a simplified view, from the rear face, of the final step of engagement.

The position and relative heights of these features on FIG. 8 enable a highly reproducible and error tolerant application of the integrated assembly to the surface of the stage. As the integrated assembly nears the stage (FIG. 9), the first element to engage (make contact) is the front alignment pin with the alignment hole of the integrated assembly. The hole has a female taper countersink to aid in alignment. As the pin engages the hole (FIG. 10), this fixes a rotation axis of the integrated assembly to the relative position of the stage. Three of the six translation degrees of freedom for the integrated package are now fixed. Next to engage (FIG. 10) is the rear pin into the alignment slot (also tapered). Engagement of these elements fixes the angle of rotation about this axis. Five of the six degrees of freedom are now fixed. As the attractive magnetic elements of the integrated package and stage are now in close proximity, the package is pulled into position against the upper surface of the stage (FIG. 7 and FIG. 11). The six degrees of freedom of the integrated assembly relative to the source mount are now fixed into place, providing highly repeatable emitter positioning on the source mount. The male, spring-loaded, voltage contact pin on the underside of the integrated package is now in full electrical contact with the female voltage receptacle of the mounting stage.

The two locking pins shown on FIGS. 6 and 8, which sit nearer to the distal end of the stage than the two alignment pins, serve to provide the function of locking the Button carriage into place when the push button of the integrated package is engaged. As described in FIGS. 4 and 5, there are no retaining elements to hold the Button carriage in the forward position within the package itself. When pressure on the button is released, the button and union carrier etc., retract to the rear position. This behavior is significantly modified by the presence of the locking pins on the mounting stage. The locking pins fit into the mating through bore's on the underside of the assembly as shown in FIG. 3. The locking pins are tall enough to make contact with the bottom surface of the button carriage. There are two mating cylindrical female indentations present on the bottom surface of the button carriage that align and mate with the locking pins when the button is pressed into the forward position and the union carrier is in contact with the stop rib inside the integrated package.

If the push button is engaged when the package is mounted on the source mount stage, when the locking pins engage with the indentation on the button carriage, the button carriage is then locked into the forward position. This is defined as the operating position, as the button carriage, union carrier, column, and nanospray emitter are in the forward position with the high-voltage contact internal to the integrated package is established. As soon as the integrated package is removed from the stage and source mount, the locking pins disengage from the underside of the integrated package. The assembly inside the package then functions as previously described herein and the emitter, column etc. return to the retracted and protected position, including disconnection of the high voltage electrical contact.

The locking pins are most preferably spring loaded from within the body of the stage, so that downward loading force on the pin causes the locking pins to retract approx. up to $4/5$ their protruding length into the body of the stage. This creates an engagement whereby the length of the locking pin installation is not an overly critical dimension and the locking feature will still function as intended. Furthermore having the pins spring-loaded ensures that the uppermost surface of the locking pin is in constant contact with the bottom surface of the button carriage as the carriage moves from the rear to the forward position. This ensures full engagement of the locking pins with the indentations on the bottom surface of the button carriage, securely locking the carriage into the operating position. The action can only be released by removing the integrated package from the surface of the stage.

The high voltage provided by the stage mount is complete through the inner components of the integrated package to the fluid contained within the coupling union. There exists a continuous electrical contact of low resistance (<100 ohms, preferably less than 10 ohms, most preferably less than 2 ohms), between the metal coupling union, the metal union carrier and the two contact pins internal to the integrated package. Thus any voltage provided by an appropriate high voltage power supply (FIG. 12) to the voltage receptacle contained within the stage of the source mount will be effectively transmitted to the fluid within the coupling union. Thus the necessary conditions (voltage etc.) for generating electrospray will be met (as described in the prior art). The high voltage to the source mount may also be provided by the mass spectrometer if so equipped.

Figure 13:
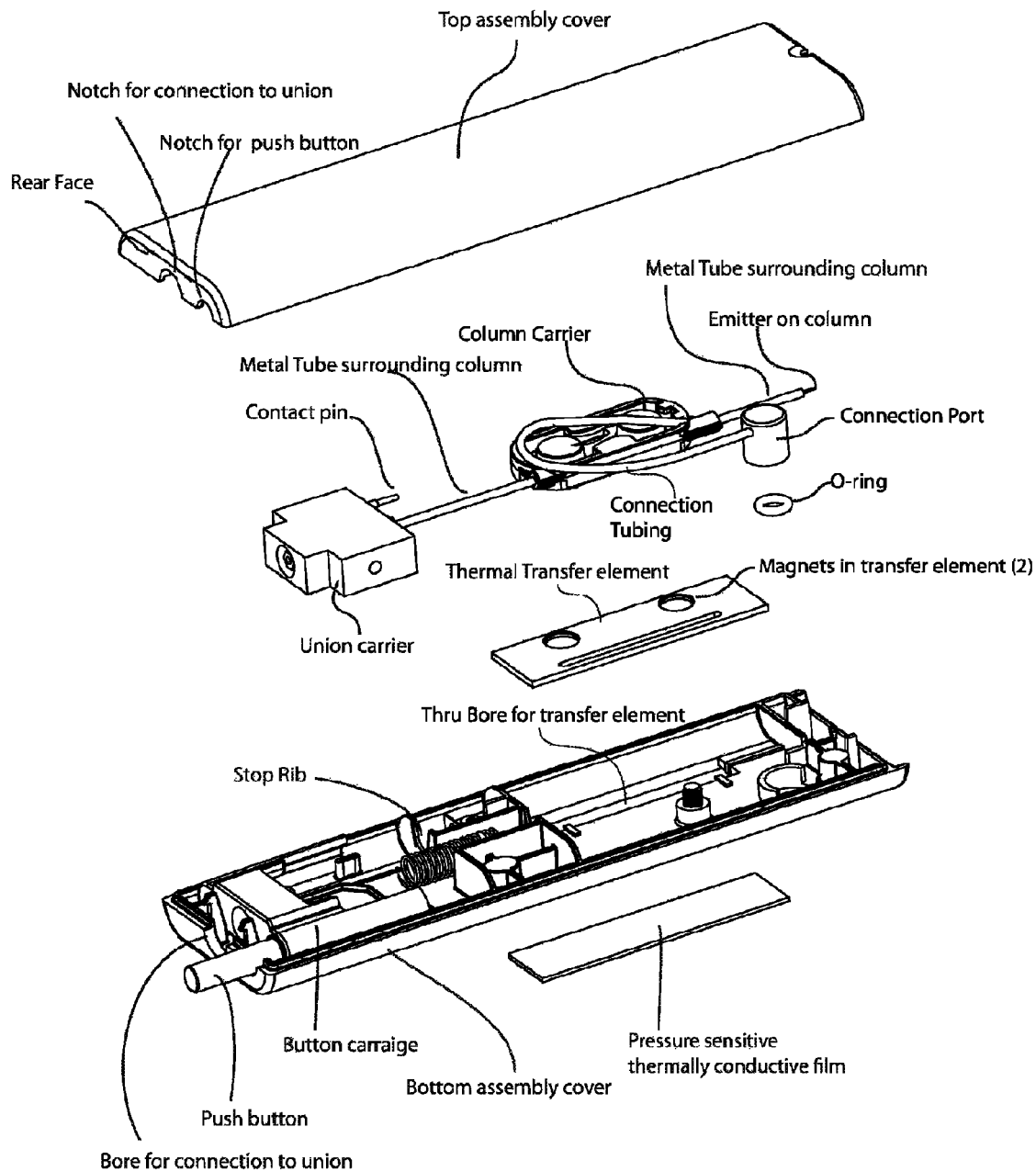
FIG. 13. is an isometric, exploded, view of an additional embodiment of the integrated nanospray package containing the column carrier, thermal transfer, and sheath gas elements.

FIG. 13 shows a particularly preferred embodiment of the integrated assembly that provides additional functionality. The additional functionality and elements includes: A column management sub-assembly (Shown in detail in FIG. 14, and schematically in FIG. 15) that provides a column carrier with the capability to hold and secure a longer column in the form of a loop or coil in combination with the ability to integrate and manage co-axial sheath gas around the proximal end of the column and nanospray emitter. The sheath gas provided by the stage mount is a complete gas-tight connection that connects to the body of the integrated source mount to the interior components of the integrated package itself (FIG. 13). This novel and inventive design takes the single metal tube of the embodiment of FIG. 1 and divides it into two sections: A proximal metal tube, and a distal metal tube. In-between the two metal tubes is a column carrier. This carrier enables the middle section of the column to be coiled in preferably an oval coil, or a "figure eight" shaped coil. The carrier contains spool and tab elements to provide for a stable wrapping of the capillary column tubing into the coil or "figure eight" shape as shown in FIG. 15. The "figure eight" shaped coil being particularly preferred since it minimizes the overall volume occupied by a given length of tubing. The interior components of the column management sub-assembly within the integrated package to supply the co-axial sheath gas are most preferably in the form of a flexible tube contained within the housing of the integrated package that provides gas tight communication between the inner bore of the the proximal metal tubing sleeve that surrounds the chromatography column and nanospray emitter and the male receiving port on the bottom assembly cover of the integrated package. The connection tubing has sufficient flexibility so as to not interfere with the sliding action of the push button assembly as the union carrier and column carrier both move from the rear to the forward and operating position. The connection tube is preferably made from a plastic material such as polyethylene, polypropylene, polyimide, or PEEK. The connection between the connection tube and column carrier may be made gas-tight through the use of compression elements such as gasket seals, o-rings, or curable adhesive materials.

Thus the gas available at the source mount through the female connection port on the upper surface of the mount's stage is transmitted through one or more internal union couplings within the integrated package to the metal tube that surrounds the nanospray emitter. This gas is then properly available to use as a so-called co-axial sheath gas to aid in nebulization of the liquid exiting the nanospray emitter. The column carrier provides the necessary gas-tight communication between the connection tube and the proximal metal sheath tube as shown in FIG. 15.

The co-axial sheath gas exits the proximal metal tube in close proximity to the nanospray emitter in-between the gap of the inside bore of the metal tube and the outer surface of the column. Typical preferred diameters for the inner bore of the proximal metal tube are 0.016" to 0.032". The outer diameter of the column is typically 0.015" to 0.018". Other relative inner and outer diameters may be suitable, including column outer diameters as large as 1/32" and metal tube inner bore sizes up to 1/16". In any case, it is critical that there is sufficient gap between these tubes to enable the flow of co-axial sheath gas at a flow rate suitable to enable nebulization of the liquid effluent.

Prior art has used coils of small diameter (fused-silica, plastic, metal) tubing to enable a long column length to be held in a smaller space. For example prior art in the field of capillary gas chromatography uses polyimide-coated fused silica tubing columns up to 25 meters long to occupy a space of only 15 cm in diameter. The inventive aspect of the embodiment described herein is that the column carrier of FIGS. 13-15, in which the column is coiled, is both (A) fabricated from a thermally conductive material and (B) is in close sliding contact with the Thermal Transfer element shown in FIG. 13. When the push button is engaged and the integrated assembly is on the stage mount, the column carrier sub-assembly moves along with the union carrier from the rear to forward (operating) position. Because the column carrier is in constant contact with the thermal transfer element during this movement, the column may be pre-equilibrated to operating temperature before the column is in the operating position. This is advantageous to speed the acquisition of system readiness and to help preserve and ensure column lifetime.

FIG. 16 shows a simplified, cross sectional view of the inventive design elements necessary to meet the needs of controlling the temperature of the nanospray emitter capillary chromatography column inside the integrated package. The mounting stage of the source mount contains a thermal control block which is preferably constructed from a material of high thermal conductivity such as aluminum or copper. Within this thermal control block is a heating, and/or cooling element, and a temperature-sensing element. The heating element is preferably a resistive cartridge heater; the cooling element is preferably a so-called thermo-electric stacked Peltier device. The temperature sensor is preferably a two wire thermocouple, resistive thermal device or, semiconductor temperature sensor. The heating/cooling elements and temperature sensor are in electrical contact and communication with a suitable closed-loop temperature control circuit and system which are well known in the art. Such a control system should enable temperature control to a precision of within 1° C. and more preferably 0.1° C. For heating it is preferable to maintain the temperature of the column within the range of 50 to 80° C.; for cooling it is preferable to be able to reduce the column to below the ambient room temperature, preferably from 4° C. to −20° C.

As shown in FIGS. 13 and 16, the thermal transfer block within the integrated package is a multi-layer device that consists of an outer layer having an applied thermally conductive pressure-sensitive adhesive film, which is preferably composed of an elastomer material loaded with a thermally conductive carrier material. A particularly preferred embodiment is a rubber gasket loaded with cerium oxide. A particularly preferred material is known by the trade name ThermaCool R-10404, that is made from a thermally conductive closed cell silicone sponge rubber. When the magnets that hold the integrated package to the stage mount are engaged, the compressive force sets the thermal transfer element and the thermal control element in thermal contact. Thus the two elements come into thermal equilibrium and the metal sheath tube and nanospray column/emitter are subsequently in thermal equilibrium with the transfer element.

Additional magnets may be preferably added to the integrated package and the source mount to increase the compressive force on the thermal gasket material. It is known that increasing the pressure between the elements from 1 to 30 pounds per square inch (psi), increases the thermal conductivity by 50%, reducing the thermal impedance of the assembly.

Prior art has typically embedded the heater and temperature sensor directly into the holder together with the capillary column and nanospray emitter. (Speers, Blackler, Wu Anal. Chem., 2007, 79 (12), pp 4613-4620). By separating these functions and using a thermally conductive heat transfer element within the body of the integrated package, this preferred embodiment enables the expensive heater/cooler and temperature sensor to reside in the (permanent) source mount. As a result this invention substantially reduces the complexity and manufacturing cost of the integrated package; which is intended to be a disposable or semi-disposable device. This embodiment also enables the sliding column carrier arrangement as shown in FIG. 13.

The chromatography column mounted inside the integrated package may be comprised and packed with chromatographic media suitable with of any and all manner of liquid chromatographic separation modes known to those skilled in the art, including: reverse phase high performance liquid chromatography, normal phase liquid chromatography, size exclusion chromatography, gel permeation chromatography, super-critical fluid chromatography, hydrophobic interaction layer chromatography, and ultra-high pressure chromatography. Column inner bore diameters preferably cover the range from 5 µm to 1 mm; and most preferably from the range of 20 µm to 250 µm. Through-column liquid phase flow rates cover the range of 1 nL/min to 100 µL/min and most preferably in the range of 10 nL/min to 2 µL/min. Hollow tubing is the preferred form of the column body contained in the integrated package. The most preferred material for the fabrication of the column body is polyimide-coated fused silica tubing, although other materials such as metal tubing or polymer tubing such as PEEK, or hybrid materials including silica lined PEEK or silica lined steel or nickel tubing are usable.

The elements of the invention are preferably designed so as to be manufactured using low-cost and high volume methods. The integrated package body and other plastic parts are preferably made by plastic injection molding. Metal parts are preferably made by high-speed computerized machining and/or metal extrusion.

Figure 12:
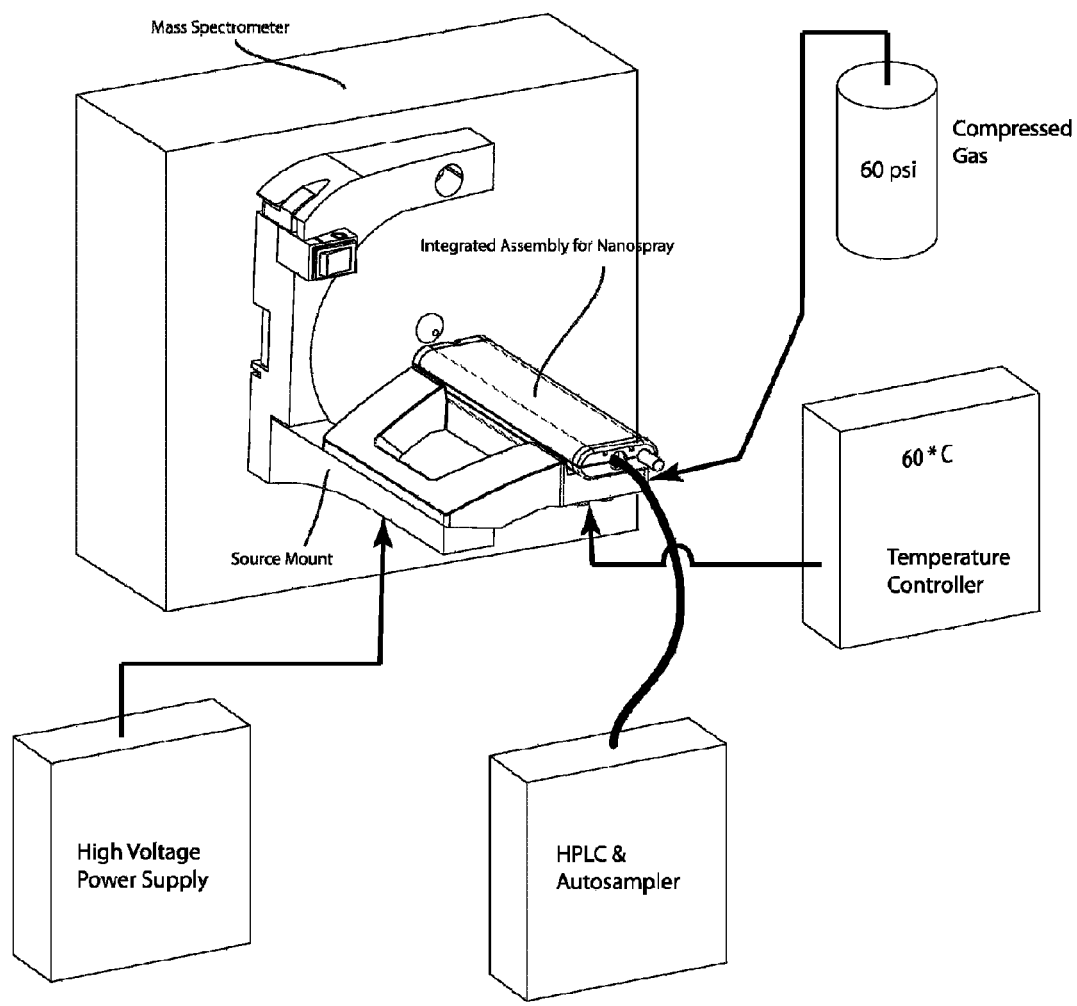
FIG. 12. is a schematic view illustrating all of the necessary systems for the desired method of use.

A total analytical system that would use the integrated nanospray package and source mount is shown in FIG. 12. When the integrated assembly is in position on the stage of the source mount and engaged with the push button in the operating position as previously described, the following conditions are met when the system is used in the context of the system of FIG. 12

Briefly the system is used as follows. Once the system shown in FIG. 12 is assembled the following conditions have been met: An integrated package has been placed on the source mount on the mass spectrometer. The stage mount is receiving a sufficient high voltage suitable for electrospray ionization (typically 2.5 kV), a suitable gas pressure (approx. 30 psi of air) for co-axial sheath gas, and the temperature control system has been engaged to regulate the temperature of the integrated package to equilibrium conditions (typically 60° C.). A suitable connection tube (PEEK or fused-silica, typically 25 to 50 µm ID) from the integrated package has been made between the coupling union inside the package and the outlet of liquid chromatography system. The liquid chromatography system is preferably capable of delivering liquid phase solvents of varying chemical composition over a wide range of flow rates, preferably in the range from 100 nL/min to 1 mL/min. The liquid chromatography system also has the capability to injection samples into the flow path. Preferable injection sizes range from 1 to 50 µL.

Samples are injected into the integrated package by the liquid chromatography system and analyzed using typical and suitable conditions for sample separation known to those skilled in the art. Analytes present in the sample, are trapped and retained on the surface of packing media contained within the chromatography column. The liquid chromatography system changes the liquid composition flowing through the column so that the desired analytes are separated and eluted from the column. As analyte elutes from the column, the high voltage delivered by the integrated package to the mobile phase in the column, causes electrospray ionization to occur as the liquid exits the nanospray emitter at the proximal end of the column. The sheath gas aids and supports this nebulization and ionization process. The fine droplets, and subsequent ions generated, are collected at the atmospheric pressure inlet of the mass spectrometer. The mass spectrometer then determines the charge-to-mass ratio of the analyte present during the elution phase. The signal generated is turned into digital data for further analysis. The chemical analysis process is complete.

The invention claimed is:

1. An integrated package for nanospray ionization, comprising
   a top assembly cover and a bottom assembly cover, which engage each other to form a package, said package having a front face a rear face, and a bottom face and containing
   a hollow tube nanospray emitter, coaxially contained in a secondary tube, having a tapered proximal end facing the front face of said package, and a distal end facing the rear face of said package,
   a column carrier having a distal and proximal end, a top side and bottom side, and configured to accommodate the coiling of lengths of nanospray emitter tubing greater than 20 cm, from the topside of the column carrier, inside the package volume,
   a tube connected to the proximal end of the column carrier through which the proximal end of the nanospray emitter protrudes,
   a rigid element connecting the distal end of the column carrier to the proximal end of said union carrier,
   a thermally conductive transfer element having a top side and bottom side, said top side being in sliding contact with the underside of said column carrier,
   a hole in the bottom package cover that permits a protrusion on the base of said thermal transfer element to be exposed to the thermal environment external to and in thermal communication with an externally applied heat or cooling source and optionally being flush with the bottom surface of the bottom package cover
   an electrically conductive, fluid-coupling union having proximal and distal ends connected by a through bore, using compression ferrules in fluid communication and sealing to the distal end of said nanospray emitter,
   an electrically conductive union carrier, having front, rear, right side and left side faces a bore through the front and rear faces, parallel to the left- and right-side faces, adapted to receive the coupling union and electrospray emitter,
   an electrical contact pin protruding from the front face of said carrier,
   a set-screw to hold the coupling union inside the bore of the union carrier,
   a push-button carriage with button element, having a cavity element facing the union carrier with protruding finger elements adjacent to the side faces of said union carrier,
   One or more indentation elements on said push button carriage facing the bottom part of the package cover,
   a limiting element contained within the package that stops forward movement of the union carrier beyond the element,
   a compression push spring between the cavity element of said push button carriage and rear face of said union carrier,
   a compression retraction spring between the front face of the union carrier and said limiting element,
   an element having an electrical contact pad in the bottom part of said package passing through a bore in the package, and enabling electrical contact of the pad with the environment external to the package,
   said package having a bore for projection of said button element,
   said package having a bore permitting the connection of external tubing to the distal side of the coupling union,
   said package having a bore in the front face of the package permitting the nanospray emitter and surrounding tube to protrude from said front face,
   said package having bores contained within the bottom cover that permit access to each of said indentation elements on said push button carriage,
   said package having two or more bores contained within the bottom cover that permit alignment of the package with a mating device,
   said push button carriage button element engaging with a first side of said union carrier through said push spring, which is in compression when said button element is pushed, to move said union carrier towards the front face of said assembly until the union carrier meets the limiting element and retracts when said button element is released, the proximal end of said electrospray emitter extending beyond the front face of said package, by optionally more than 1 millimeter, and said contact pin on the union carrier is in electrical contact with said contact pad, said indentations on said carrier then being aligned with said bore holes on the package bottom cover,
   said retraction spring being engaged with a second side of said union carrier and in opposition to said push spring, so that when said push spring is relaxed said retraction spring forces said union carrier away from said front face of said assembly and towards the rear face of said assembly, said electrospray emitter is pushed back and fully contained within the body of said package, with said proximal end being more than 1 mm behind the front face of the package.

2. A nanospray mass spectrometer source mounting system for the integrated nanospray ionization package of claim 1 comprising
a mounting stage having proximal and distal ends, with the proximal end adapted to face the inlet of a mass spectrometer having a high voltage supply, and the distal end to face away from the inlet of said mass spectrometer, having a top mounting surface, with protruding edge guide rails and left and right sides of the top mounting surface,
one or more guide pins rigidly mounted into, and protruding from the top mounting surface of said mounting stage, optionally lower in overall height than said guide rails,
an electrical contact receptacle, connected to the high voltage power supply of the mass spectrometer,
one or more magnets having top surfaces embedded in the top mounting surface of the mounting stage, optionally with said top surface of said one or more magnets below flush of said top surface of the mounting stage,
two or more retracting and spring-loaded locking pins protruding from the top surface of mounting stage, towards the distal end of the mounting stage, protruding to a height above said top surface just below the height of the guide pins when no pressure is applied to said pins, when pressure is applied to the pins in a direction normal to the top surface of said mounting stage, said pins being retracted and approximately flush with said top surface.

3. The package of claim 1, wherein the nanospray emitter tube comprises
a chromatography column having a porous chromatographic bed containing a surface bound stationary phase, with a proximal and distal end; the proximal end being the outlet of the column and having an integral tapered nanospray emitter, the distal end of the column being connected to the outlet of said coupling union.

4. The package of claim 3, wherein the chromatography column bed is comprised of porous or semi-porous packed silica particles, having a diameter of 5 µm or less, with the porous or semi-porous silica having a surface coated with an organic stationary phase coating, the column having an internal diameter of 500 µm or less, and a bed length greater than 2 cm.

5. The package of claim 3, wherein the chromatographic bed is comprised of cast monolithic porous polymer or monolithic porous silica, having a column diameter of 500 µm or less, and a bed length greater than 2 cm.

6. The package of claim 1, further comprising
a gas-tight receiving port in the bottom cover having an inlet and outlet, the inlet of the port being flush with the bottom surface of the bottom cover,
the tube surrounding the nanospray emitter having an internal diameter that is 100 µm or more than the outside diameter of the nanospray emitter,
a hollow, flexible tube connecting the outlet of said receiving port to the inner bore of said tube surrounding the nanospray emitter,
whereby when pressurized gas is admitted to the receiving port, said pressurized gas flows through the connecting tube and subsequently through the tube surrounding the nanospray emitter, said gas exiting within 1 millimeter of the proximal end of the nanospray emitter.

7. The package of claim 6, wherein the nanospray emitter tube comprises
a chromatography column having a porous chromatographic bed containing a surface bound stationary phase, with a proximal and distal end; the proximal end being the outlet of the column and having an integral tapered nanospray emitter, the distal end of the column being connected to the outlet of said coupling union.

8. The package of claim 1, further comprising
a gas-tight receiving port in the bottom cover having an inlet and outlet, the inlet of the port being flush with the bottom surface of the bottom cover,
the tube surrounding the nanospray emitter having an internal diameter that is 100 µm or more than the outside diameter of the nanospray emitter,
a hollow, flexible tube connecting the outlet of said receiving port to the inner bore of said tube surrounding the nanospray emitter,
whereby when pressurized gas is admitted to the receiving port, said pressurized gas flows through the connecting tube and subsequently through the tube surrounding the nanospray emitter, said gas exiting within 1 millimeter of the proximal end of the nanospray emitter.

9. The nanospray mass spectrometer source mounting system and mounting stage of claim 2 further comprising
a port for delivering pressurized gas on the top-mounting surface of said mounting stage, said port being in gas communication with the pressurized gas delivered by the mass spectrometer, or optionally though an independent source of pressurized gas,
a temperature controlled, thermally conductive, thermal control block, on the top-mounting surface of said mounting stage, said block being connected to an external electronic temperature controller and containing an electrically resistive heating element, and optionally an electrical cooling element, said block being mounted sub-flush of the top-mounting surface, and held below the surface plane by compression springs, magnets mounted in the thermal control block permitting the block to raise above the level of the top surface when the magnetic attraction to a mating device placed on or near the mounting stage overcomes the spring force, thus ensuring thermal contact between the heating element and a said mating device.

10. A system for mass spectrometry comprising
a mass spectrometer having provisions for high voltage and pressurized gas flow systems for the production of electrospray ionization,
an integrated nanospray ionization package of claim 6,
a mounting stage for said nanospray ionization package,
said mounting system being rigidly connected to said mass spectrometer and interfacing with said high voltage and positioning the nanospray package in position for collection by the mass spectrometer of ions generated by the package,
said nanospray package being placed on said mounting stage and held in place by magnets, the alignment of the package being determined by the elements on the stage, electrical contact between the package and stage is established when the push button of the package is pressed, with the locking elements on the stage holding the nanospray emitter in position, and the high-voltage being engaged.

11. A system for mass spectrometry comprising
a mass spectrometer having provisions for high voltage and pressurized gas flow systems for the production of electrospray ionization, an integrated nanospray ionization package of claim 8,
a mounting stage for said nanospray ionization package,
said mounting system being rigidly connected to said mass spectrometer and interfacing with said high voltage and pressurized gas systems, positioning the nanospray package in position for collection by the mass spectrometer of ions generated by the package,
said nanospray package being placed on said mounting stage and held in place by magnets, the alignment of the package being determined by the elements on the stage, as is the gas connection, electrical contact between the high-voltage, package and coupling union is established, when the push button of the package is pressed, with the locking elements on the stage holding the nanospray emitter in position, and the thermal transfer block of said package is in direct contact with a thermal control block capable of heating, or optionally cooling, being present on the mass spectrometer mount.

* * * * *

UNITED STATES PATENT AND TRADEMARK OFFICE
CERTIFICATE OF CORRECTION

PATENT NO. : 9,646,815 B2  
APPLICATION NO. : 14/409233  
DATED : May 9, 2017  
INVENTOR(S) : Valaskovic et al.

Page 1 of 1

It is certified that error appears in the above-identified patent and that said Letters Patent is hereby corrected as shown below:

In the Specification

Column 4, Line 46, "it's" should read -- its --

Column 7, Line 37, "bore's" should read -- bores --

Signed and Sealed this
Tenth Day of December, 2019

Andrei Iancu
*Director of the United States Patent and Trademark Office*